United States Patent [19]

Bowditch et al.

[11] Patent Number: 4,603,076

[45] Date of Patent: Jul. 29, 1986

[54] HYDROPHILIC FOAM

[75] Inventors: W. Raymond Bowditch, West Chester; Borys Rybalka, Philadelphia, both of Pa.

[73] Assignee: Norwood Industries, Inc., Malvern, Pa.

[21] Appl. No.: 707,955

[22] Filed: Mar. 4, 1985

[51] Int. Cl.$^4$ ............................................. B32B 5/18
[52] U.S. Cl. .................... 428/246; 128/156; 428/316.6; 428/317.1; 428/319.1
[58] Field of Search ............. 128/82, 132 D, 156; 604/369; 428/246, 304.4, 316.6, 317.1, 317.5, 317.7, 319.1

[56] References Cited

U.S. PATENT DOCUMENTS

| 3,883,571 | 5/1975 | Allport et al. | 260/453 AM |
|---|---|---|---|
| 3,890,254 | 6/1975 | Guthrie | 521/159 |
| 4,049,592 | 9/1977 | Marans et al. | 521/159 |
| 4,132,839 | 1/1979 | Marans et al. | 521/159 |
| 4,137,200 | 1/1979 | Wood et al. | 521/159 |
| 4,216,177 | 8/1980 | Otto | 264/25 |
| 4,260,440 | 4/1981 | Frankenberg | 428/246 |
| 4,263,412 | 4/1981 | Pauls | 521/114 |
| 4,273,913 | 6/1981 | Wood et al. | 528/77 |
| 4,292,412 | 9/1981 | Wood | 521/107 |
| 4,365,025 | 12/1982 | Murch et al. | 521/159 |

FOREIGN PATENT DOCUMENTS 1306372 1/1970 United Kingdom .

OTHER PUBLICATIONS

Hypol Plus Formable Hydrophilic Prepolymers Technical Bulletin, Laboratory Procedures and Foam Formulations, Organic Chemicals Division, W. R. Grace & Co.

*Primary Examiner*—William J. Van Balen
*Attorney, Agent, or Firm*—Webb, Burden, Robinson & Webb

[57] ABSTRACT

MDI-based prepolymers are blown with a substantially nonaqueous blowing agent, such as pressurized air, an polymerized with stoichiometric amounts of polyoxyethylene polyol having at least two hydroxyl equivalents per mole, yielding a hydrophilic foam. The present foams may be extruded, knife-coated or otherwise cast into sheets, or may be fabricated by other known foam preparation techniques. Because the foam is polymerized with polyoxyethylene polyol instead of water, the foam exhibits both superior drape and improved stretch and recovery as compared with prior-art MDI-based flexible foams formed with aqueous reactants. The foam is particularly suited for use in external biomedical applications as, for example, a laminated medical/surgical dressing in which a thin sheet of the hydrophilic foam adheres to a nonstick aluminized veil on one side.

5 Claims, No Drawings

HYDROPHILIC FOAM

FIELD OF THE INVENTION

The present invention relates generally to polyurethane foams and specifically to an easy-to-handle system for preparing improved hydrophilic flexible foams which demonstrate superior drape, stretch and recovery. The foams of the present invention are particularly suited for use in external biomedical applications.

DESCRIPTION OF THE PRIOR ART

To those familiar with the commercial production of polyurethane foams, the chemistry of the aqueous 2-stage (prepolymer) process is well known. A urethane prepolymer (the reaction product of an isocyanate and a polyol) is reacted with water to generate carbon dioxide. The carbon dioxide functions as the blowing agent while simultaneous chain extension and crosslinking cures the prepolymer into a polyurethane foam. The aqueous 2-stage process has persisted as a foaming technique of significant commercial importance for over three decades.

A particular family of polyurethane prepolymers, derived from methylenediphenyl diisocyanate (MDI) and sold under the trademark HYPOL PLUS, was developed by W. R. Grace & Company for use in the aqueous 2-stage process of foam production. These prepolymers, and the aqueous 2-step process foams produced therefrom, are disclosed in U.S. Pat. No. 4,365,025 to Murch et al., which discloses an isocyanate containing prepolymer in which the isocyanate is a mixture of MDI and polymeric forms of MDI. The prepolymer is foamed by mixing it with an approximately equal amount of water. The resultant flexible foams are characterized by greater hydrolytic stability than those foamed from tolylene diisocyanate (TDI) prepolymers, and the MDI-based foams may be made without the toxin/carcinogen hazards associated with residual TDI in the workplace.

The product is difficult to handle, however, due to the large volume of aqueous reactant necessary and due to the high speed of the reaction. Production equipment must be designed to accommodate the introduction of a substantial quantity of water, must be equipped to evaporate the unreacted portion of the aqueous component (requiring additional energy in the form of heat) and must be capable of producing foamed products larger than needed to accommodate the severe and uneven shrinking which occurs during evaporation. Such production equipment is expensive both to design and to use. In addition, because a maximum of a few minutes is available for fabrication between the time and reactants first commingle and the tackfree cure of the final foam, the product is limited to such uses as mold casting and foamed-in-place operations and is wholly unsuited to such fabrication techniques as the extrusion and knifecoating processes. For example, none of the MDI-based prepolymers disclosed in U.S. Pat. No. 4,365,025 to Murch et al. can be mixed with water and fabricated into a thin foam sheet with a Gardner (or other suitable) knife: the foam rises and cures long before a thin sheet material can be cast.

Prior to the development of the prepolymers disclosed in Murch et al., a method was developed for avoiding the handling problems inherent in the 2-stage prepolymer process. British Pat. No. 1,306,372 to Marlin et al. teaches a method of mixing an isocyanate with a reactive hydrogen compound in the presence of an organosilicon surfactant, and frothing the mixture with pressurized inert gas. The organosilicon surfactant prevents the foam from curing by imparting chemical and structural stability to the froth until the foam is cured by heating. Only latent metal catalysts may be used in the Marlin et al. process, i.e., those tin and nickel and other metal catalysts for which organosilicon surfactants act as synergistic inhibitors at ambient temperatures without inhibiting catalytic activity at elevated temperatures. In addition to its other chemical properties, the organosilicon surfactant consistently imparts a hydrophobic character to the final cured product.

Accordingly, the Marlin et al. process is wholly unsuited for use in the preparation of hydrophilic foams from the Murch et al. prepolymers not only because the Marlin et al. method requires undesirable elevated-temperature curing and permits only limited uses of surfactants and catalysts, but because the method cannot yield a hydrophilic foam at all in the presence of organosilicon. A need thus remains for a method of producing an MDI-based flexible hydrophilic foam which is wellsuited for use in all types of fabrication techniques and applications, and yet which avoids the disadvantages of the aqueous 2-stage prepolymer process and the formulational and end-product limitations of the Marlin et al. technique.

SUMMARY OF THE INVENTION

Without the need for aqueous reactants or organosilicon surfactants and the limitations they impose, the present invention provides a method for preparing a hydrophilic foam by blowing an MDI-based prepolymer with a substantially nonaqueous blowing agent, such as pressurized air, and polymerizing the prepolymer with a polyoxyethylene polyol having at least two hydroxyl equivalents per mole. The present method permits the hydrophilic foam to be extruded, knifecoated or cast into sheets, as well as to be fabricated by other known foam preparation techniques, and thus is suitable for use in any flexible foam operation. Hydrophilicity is controlled with an appropriate nonorganosilicon surfactant if a surfactant is used at all, and cure may proceed at ambient or elevated temperatures as desired. In addition, because the foam is prepared with polyoxyethylene polyol instead of water, the foam exhibits both superior drape and improved stretch and recovery as compared with prior art MDI-based aqueous 2-stage flexible foams.

DETAILED DESCRIPTION OF THE INVENTION

The prepolymers from which the present foams are prepared are based on diphenylmethane diisocyanates (for which the common name is methylenediphenyl diisocyanate, or MDI) and are fully disclosed in U.S. Pat. No. 4,365,025 to Murch et al., incorporated herein by reference. The prepolymers are isocyanate-capped polyols or mixtures of polyols wherein the isocyanate mixture has a functionality of greater than 2.0; the prepolymer is a mixture of diphenylmethane diisocyanate and polymethylene polyphenyl isocyanate. The prepolymer is mixed with a stoichiometric amount of polyoxyethylene polyol, along with certain optional additives, and a substantially nonaqueous blowing agent foams the mixture as it reacts. Because the foamed products of the present invention are polymerized with polyoxyethylene polyol instead of water, the foams cure at a lower rate than those prepared by the aqueous 2-stage process, yielding a liquor prepolymer/polyol system which cures quickly enough for commercial use, with or without heat curing and with or without a catalyst, yet slowly enough to permit the fabrication of foam products by all known foam fabrication methods, including knife-coating, extrusion and similar techniques.

The prepolymer and the polyoxyethylene polyol may be mixed together by any mechanical mixing arrangement which will insure complete mixing, such as by mixing in a tank with a high-speed stirrer, by spraying, or by the use of conventional mixing and metering machinery of the polyurethane industry such as the variable speed mixing head. The various additives are combined with one or the other of the two phases (the prepolymer phase or the polyol phase) prior to mixing. As the two phases are mixed, the substantially nonaqueous blowing agent causes the prepolymer/polyol system to rise, and foaming and curing proceed at a rate which yields a prepolymer/polyol reaction product in the form of an open-celled flexible polyurethane foam.

Suitable polyoxyethylene polyols are those having at least about 50% by weight oxyethylene groups. Among the diols are polyethylene glycol type diols having molecular weights from about 200 to about 6,000, such as 3,6,9 trioxaundecane 1,11 diol (for which the common name is tetraethylene glycol) having a molecular weight of 194. A variety of suitable polyoxyethylene polyols may be obtained by the chemical addition, known in the art, of ethylene oxide or mixtures of ethylene oxide and propylene oxide to water or polyhydric compounds. The polyoxyethylene triols include, among many, 3,6,9 trioxaundecane 1,7,11 triol. The polyoxyethylene polyol may also be a compound having a functionality of greater than 3, although for reasons of economy and handling the polyoxyethylene polyol is preferably a polyoxyethylene diol or triol. The amount of polyoxyethylene polyol employed, as compared with the prepolymer, will vary slightly depending upon the nature of, and the end use for, the foam being prepared. In general, the total hydroxyl hydrogen equivalents should be such as to provide a ratio of 0.8 to 1.2 equivalents of isocyanate per equivalent of hydroxyl hydrogen, and preferably a ratio of 0.9 to 1.1 equivalents of isocyanate per equivalent of hydroxyl hydrogen. The ratio of isocyanate to hydroxyl hydrogen, therefore, will always be about 1:1. Foams produced for medical/surgical uses should always be formulated with no more than 1.0 equivalent of isocyanate per 1.0 equivalent of hydroxyl hydrogen to eliminate residual unreacted isocyanate (and its associated cytotoxicity) from the final product.

Pressurized air is a suitable nonaqueous blowing agent for use in the present invention, as are other pressurized gases inert to the urethane polymerization reaction. As the prepolymer and polyol phases are mixed, pressurized air may be injected into the mixture by means of an air pump, or other source of pressurized air, in combination with a suitable air intake valve in the mixing apparatus. If the air is mixed into the prepolymer/polyol system, the air divides into a dispersion of air bubbles which is partially responsible for the cellular structure in the cured foam. The pressurized air need not be entirely nonaqueous but need be only substantially nonaqueous: although water vapor in the air might react with available isocyanate to generate carbon dioxide and result in a minor number of urea linkages in the cured foam, the presence of a minor amount of water vapor will not appreciably increase the rate of cure of the foam or measurably affect the properties of the final product.

Low-boiling point liquids (containing little or no water) are also suitable as substantially nonaqueous blowing agents for the purposes of the present invention. These low-boiling point liquids are used in place of or in conjunction with the injection of pressurized air into the prepolymer/polyol system. Suitable low-boiling point liquids include esters, ketones, alkanes, chlorinated hydrocarbons and benzene derivatives. Toluene is useful as a blowing agent, as are the lower alkyl acetates such as ethyl acetate. Other suitable low-boiling point liquids are fluorotrichloromethane, dichlorodifluoromethane and methylene chloride. These low-boiling point liquids, after incorporation into the prepolymer/polyol system, expand upon heating to result in commensurate expansion of the polyurethane before and during cure. The low-boiling point liquids must be substantially nonaqueous in like manner as the pressurized air blowing agent, i.e., no more than a minor amount of water may be present in the blowing agent as it is added to the prepolymer/polyol system.

Because a substantially nonaqueous blowing agent is added to the prepolymer/polyol system, and because the prepolymer/polyol system itself is substantially nonaqueous, the urea linkages characteristic of aqueous 2-stage process foams are largely absent from the present invention. As a result, the present product is a true urethane system wherein the linkages are predominantly or exclusively urethane linkages. In theory, although applicant does not intend to be bound by such a theory, this true polyurethane system, substantially lacking in polyurea, yields the superior drape, stretch and recovery characteristic of the present polyurethane foam due to the relatively higher bond strength of urethane linkages as compared with urea linkages found in aqueous 2-stage process foams. (By contrast, flexible polyurethane foams containing polyurea are more brittle than those of the invention.) Furthermore, because the polyoxyethylene polyol has at least about 50% by weight oxyethylene groups, and the MDI-prepolymer likewise contains at least about 50% by weight oxyethylene groups, the final foam has consistent elastomeric strength throughout due to oxyethylene uniformity, contributing to the superior stretch and recovery.

Although the polyurethane foams of the present invention are hydrophilic per se when formulated without surfactant or with a suitable surfactant, additional hydrophilic compounds may be incorporated into the foam to increase its capacity to absorb aqueous liquids. These hydrophilic compounds include derivatives of silica, natural and artificial fibers and hydrophilic polymers. In particular, a useful hydrophilic polymer is the copolymer of 2-propenoic acid (the common name for which is acrylic acid) and the potassium salt of 2-propenoic acid, a white powder manufactured by Arakawa Chemical (USA) Inc. and sold under the U.S. Registered Trademark ARASORB. The 2-propenoic acid copolymer is suitable for use as an absorbent additive in the present polyurethane foam because it holds over 800 times its weight in water. The ARASORB powder may be used with or without preliminary ball milling to reduce particle size, and may be incorporated into the prepolymer/polyol system by premixing it with the polyol phase. Preferably, however, the ARASORB is ball milled to a mesh screen between 100 and 400 before use. Up to about 3 parts by weight ARASORB may be mixed with about 1 part by weight polyol in the preparation of the polyol phase of the system. The ARASORB may also be added to the prepolymer phase, before the two phases are mixed.

A catalyst may be incorporated into the prepolymer/polyol system by premixing it with the polyol phase. (The catalyst may also be premixed with the prepolymer phase, but only immediately before the prepolymer and polyol phases are added together.) The catalyst is added in any amount which yields an open-celled flexible foam and, accordingly, all but high concentrations of catalyst may be used if a catalyst is used at all. The most common suitable catalysts are the tertiary amines, such as the alkyl morpholines, triethylamine and a number of diamines, although organometallic compounds are also suitable catalysts for the present reactive system. In particular, suitable catalysts include n-methyl morpholine, n-ethyl morpholine, trimethylamine, triethylamine, tetramethyl butane diamine, triethylene diamine, dimethylaminoethanol, benzyldimethylamine, dibutyl tin dilaureate and stannous octoate. The preferred catalysts are triethylamine and trimethylamine.

The surfactant may be incorporated into the prepolymer/polyol system by premixing it with either phase, and preferably with the polyol phase. Any anionic, cationic, nonionic or amphoteric surfactant may be used as long as it does not yield a hydrophobic product; organosilicon and fatty ester surfactants may not be used in the present invention. The surfactant may be added in an amount up to about 10 parts by weight based upon 100 parts by weight of the prepolymer/polyol system. Suitable surfactants include sorbitan trioleate, polyoxyethylene sorbitol oleate, polyoxyethylene sorbitan monolaureate, polyoxyethylene lauryl ether, polyoxyethylene stearyl ether, fluorochemical surfactants such as Zonyl FSN by E. I. du Pont and Fluorad FC 170C by 3M, and block copolymer condensates of ethylene oxide and propylene oxide with propylene glycol, such as the PLURONIC surfactants available from BASF Wyandotte.

Although the present MDI-based polyurethane foams are suitable for use in all flexible polyurethane foam applications, the foams have particular utility in biomedical applications. The foam is well suited for use in anatomic supports and wound dressing materials both because it is hydrophilic and because it can withstand steam autoclave sterilization and attack by solvents and microbes. Furthermore, due to the unlimited fabrication methods available to prepare the present hydrophilic foams, the foams may be either cast in molds or knife-coated or otherwise fashioned directly into sheets for use in wound or surgical dressings. Foam sheets may also be prepared by foaming a polyurethane slab or bun and skiving (knife-splitting) it by continuously paring the outer surface of the bun. Sheets having uniform cell size throughout may be prepared either by skiving or by direct sheet casting, and sheets having a gradient cell size may be cast by decreasing the amount of catalyst in the system. Three-dimensional anatomic supports and other three-dimensional structures may be carved from foam buns or foamed directly into a mold.

The hydrophilic foam sheets of the invention may be used alone as a bandaging material, or may be used in combination with other materials to form a layered bandage or dressing. The present hydrophilic foam may be incorporated into any layered dressing in which an absorbent layer is necessary or desirable, and may be incorporated into transdermal drug delivery systems. The hydrophilic foam is particularly useful in combination with an aluminized veil, which is a gauze or other porous substrate onto which has been vacuum deposited a biologically inert aluminum coating. Aluminized veils are known in the art and are available from Lohmann GmbH & Co., KG. When the hydrophilic foam sheet is laminated with the aluminized veil and the aluminized side of the laminate is placed adjacent a wound, the aluminized veil increases the nonstick properties of the dressing and accordingly broadens its overall medical utility. The foam may be cast directly onto the aluminized veil or may be laminated with the aluminized veil by means of moisture vapor permeable or porous adhesives known in the art.

The subject foams may be cured at ambient or elevated temperatures, although elevated temperatures minimize curing time. Specifically, the present foams should be cured in an oven or other chamber maintained between about 20° C. and 200° C. for a few minutes to 24 hours, and preferably between about 40° C. and 180° C. for 2 minutes to 8 hours. Lower and higher cure temperatures than those specified may be used, but excessively low temperatures may yield an unacceptably slow rate of cure if low quantities of catalyst are used, and excessively high temperatures may cause discoloration.

The following examples illustrate specific embodiments of and methods for making and using the invention.

EXAMPLE I

A polyol phase was mixed in a suitable laboratory vessel containing 6.8 g. 3,6,9 trioxaundecane 1,11 diol (tetraethylene glycol), 1.0 g. PLURONIC L-62 surfactant, 10.4 g. ethyl acetate, 3.5 g. toluene and 19.9 g. 100 mesh screen ARABSORB (2-propenoic acid copolymer) powder. A prepolymer phase was charged to a separate vessel, and contained 47.1 g. HYPOL PLUS 4000 (a diphenylmethane diisocyanate containing isocyanate product with a functionality of greater than 2 comprising a mixture of diphenylmethane isocyanate and a polymethylene polyphenyl isocyanate). Four drops of triethylamine (0.4 ml., approximately 0.4 g.) were added, with stirring, to the polyol phase and immediately thereafter both the polyol and prepolymer phases were charged to a mixing vessel and mixed at high speed for two minutes. The mixed prepolymer/polyol system was discharged and was knife-coated onto a release liner by a coating knife set to a 0.080 mil elevation from the release liner. The release liner was transferred to an oven and cured for 5 minutes at 110° C. and for 10 minutes at 153° C. A cured foam sheet resulted having good appearance and superior drape, stretch and recovery. The foam was removed from the release liner and samples of the foam were floated on the surface of a vessel containing distilled water. When the liner side of the foam contacted the distilled water, the foam became saturated with water after 10-15 seconds. When the skin of the sample contacted the surface of the water, saturation was complete after 3 minutes.

EXAMPLE II

The following were charged to a suitable laboratory vessel to yield a polyol phase: 136 g. 3,6,9 trioxaundecane 1,11 diol (tetraethylene glycol), 20 g. PLURONIC L-62 surfactant, 208 g. ethyl acetate, 70 g. toluene, and 398 g. ARASORB (2-propenoic acid copolymer) powder ground to 100 mesh. Approximately 8 g. of triethylamine were added, with stirring, to the polyol phase. The prepolymer, 942 g. of HYPOL PLUS 4000, and the polyol phase were then transferred to a mixing vessel and the prepolymer/polyol system was mixed at high speed for 4 minutes. Air was introduced into the prepolymer/polyol system during mixing.

A rectangular aluminum mold (16¾"×12"×1½") was lined with release paper. The prepolymer/polyol system was discharged evenly into the mold. The foam was permitted to expand at room temperature for 15 minutes, after which the foam was removed to an oven to cure for 3 hours at 108° C. and ½ hour at 153° C., sequentially. The foam was skived into a continuous sheet approximately 0.04 (±0.005) mils thick. Water absorption in samples of the foam was complete, from either side of the foam sheet, after 15 seconds.

EXAMPLE III

A thin foam sheet was prepared by the same method as in Example II, except that approximately 8 g. of triethylene diamine were substituted for the 8 g. triethylamine. Tack-free cure of the foam was completed after 10 minutes in a 115° C. oven, and the resultant foam sheets were more fine-celled in structure than the foams of Example II.

I claim:

1. A foam laminate, comprising:
   an aluminized veil laminated with a foam layer, said foam layer further comprising the blown reaction product of:
   (a) a diphenylmethane diisocyanate-containing isocyanate product with a functionality of greater than 2 comprising a mixture of diphenylmethane diisocyanate and polymethylene polyphenyl isocyanate; and
   (b) a polyol having at least about 50% by weight of oxyethylene groups and having at least two hydroxyl equivalents per mole, the ratio of the isocyanate equivalents to the total hydroxyl equivalents being about 1:1;
   wherein said foam layer incorporates a surfactant, a catalyst, and a means for absorbing aqueous liquid.

2. The foam laminate of claim 1, wherein said means for absorbing aqueous liquid is a copolymer of 2-propenoic acid and 2-propenoic acid potassium salt.

3. The foam laminate of claim 2, wherein said foam layer is laminated with said aluminized veil by means of an adhesive.

4. The foam laminate of claim 3, wherein said adhesive is moisture vapor permeable.

5. The foam laminate of claim 4, wherein said adhesive is porous.

* * * * *